(12) United States Patent
Warp

(10) Patent No.: US 8,401,256 B2
(45) Date of Patent: Mar. 19, 2013

(54) SYSTEMS AND METHODS FOR AN INTERACTIVE PACS IMAGE DISPLAY TEST IMAGE

(75) Inventor: Richard Jon Warp, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1154 days.

(21) Appl. No.: 11/559,188

(22) Filed: Nov. 13, 2006

(65) Prior Publication Data

US 2008/0112601 A1    May 15, 2008

(51) Int. Cl.
*G06K 9/00* (2006.01)
*G06K 9/40* (2006.01)

(52) U.S. Cl. ........ 382/128; 382/129; 382/130; 382/131; 382/132; 382/274

(58) Field of Classification Search .......... 382/128–132, 382/274; 707/104.1, 10
See application file for complete search history.

(56) References Cited

U.S. PATENT DOCUMENTS

| | | | |
|---|---|---|---|
| 5,600,574 A * | 2/1997 | Reitan | 702/185 |
| 6,333,991 B1 * | 12/2001 | Schreiber et al. | 382/132 |
| 6,731,783 B2 * | 5/2004 | Tsujii | 382/132 |
| 7,249,329 B1 * | 7/2007 | Baeckler et al. | 716/3 |
| 2005/0018894 A1 * | 1/2005 | Couwenhoven et al. | 382/132 |
| 2006/0072799 A1 * | 4/2006 | McLain | 382/128 |
| 2006/0177114 A1 * | 8/2006 | Tongdee et al. | 382/128 |
| 2007/0116336 A1 * | 5/2007 | Mahesh et al. | 382/128 |

OTHER PUBLICATIONS

Ehsan S. ("Assessment of display performance for medical imaging systems: Executive summary of AAPM TG18 report", Med. Phys. 32(4), Apr. 2005, pp. 1205-1224, Am Assoc. Phys. Med.).*
SMPTE—http://www.smpte.org/.
NEMA-DIC—http://medical.nema.org/.
ISO 9241 & 13406—http://www.iso.org/.
VESA Standard—http://www.vesa.org/.
IHE—http://www.ihe.net/.
GB/T 17006.5-2000—http://webstore.ansi.org/ansidocstore/product.asp?sku=GB/T+17006.5-2000.
Ehsan Samei, Assessment of Display Performance for Medical Imaging Systems: Executive Summary of AAPM TG18 Report, Med. Phys. 32 (4), Apr. 2005, pp. 1205-1224, Am. Assoc. Phys. Med.

* cited by examiner

*Primary Examiner* — Vu Le
*Assistant Examiner* — Amara Abdi

(57) ABSTRACT

Certain embodiments of the present invention provide a test image including a plurality of bands and a plurality of markers in each band. Each band includes a plurality of pixels of the same pixel value. Each marker contrasts with the plurality of pixels in the band. The markers are adapted to allow a user to determine a feature of an image display system.

9 Claims, 2 Drawing Sheets

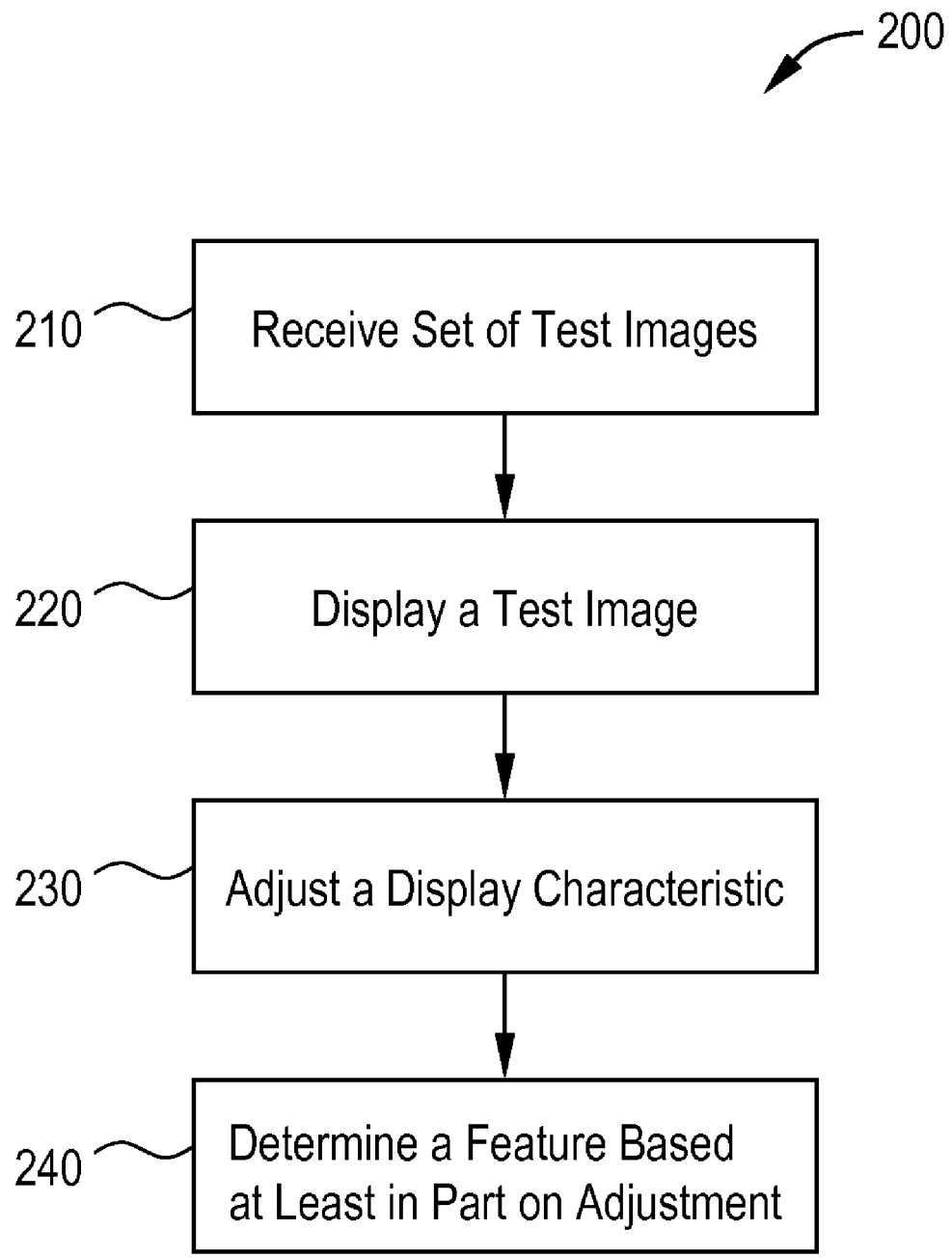

SYSTEMS AND METHODS FOR AN INTERACTIVE PACS IMAGE DISPLAY TEST IMAGE

BACKGROUND OF THE INVENTION

The present invention generally relates to medical imaging. In particular, the present invention relates to systems and methods for an interactive picture archiving and communication system (PACS) image display test image.

PACS connect to medical diagnostic imaging devices and employ an acquisition gateway (between the acquisition device and the PACS), storage and archiving units, display and review workstations, databases, and sophisticated data processors. These components are integrated together by a communication network and data management system. A PACS has, in general, the overall goals of streamlining healthcare operations, facilitating distributed remote examination and diagnosis, and improving patient care.

A typical application of a PACS system is to provide one or more medical images for examination by a medical professional. For example, a PACS system can provide a series of x-ray images to a display workstation where the images are displayed for a radiologist to perform a diagnostic examination. Based on the presentation of these images, the radiologist can provide a diagnosis. For example, the radiologist can diagnose a tumor or lesion in x-ray images of a patient's lungs. Thus, it is highly desirable that the digital images be correctly displayed.

Acquisition modalities, such as digital x-ray (DX), computed tomography (CT), and magnetic resonance (MR), may be configured in various ways to send images to the PACS. For example, different modalities from different vendors may use different send and/or transfer orders and/or different image formats. In addition, PACS and review workstations may be configured in various ways to receive and display images. For example, the PACS workstation may be configured to display images according to a set of hanging protocol rules that control image appearance.

A common format used for medical images is the Digital Imaging and Communications in Medicine (DICOM) format. The DICOM format consists of two aspects, the image pixel data and the DICOM header tag elements. DICOM images often contain look-up tables (LUTs) that are used to display medical images. The LUTs may be applied to the image pixel data and/or in the header tag elements of a DICOM image. The LUT may be used to provide a mapping from an image pixel value to a display brightness. That is, a LUT may affect the way an image is displayed.

PACS and review workstations often fail to display medical images correctly. For example, they may not apply a LUT included in the DICOM header; display or use incorrect brightness and/or contrast values; apply a separately unspecified LUT; apply a LUT incorrectly; apply a LUT, but may not interactively update the image display when the user changes the brightness and/or contrast; not offer options of which LUT to display if multiple LUTs are included; not allow the user to view DICOM header information; and/or have unintended interactions in the image display based on collimation, annotations, or other image features.

A common cause of difficulties with image display on PACS workstations is that the DICOM rules are not clearly defined and may be interpreted in different ways. For example, the DICOM rules for the value-of-interest LUT (VOI-LUT) do not clearly state how a PACS should respond when a user changes brightness or contrast.

Another cause of difficulties is that many DICOM formats exist, such as DX, CT, and MR. In addition, there are many medical imaging modality vendors and many medical imaging PACS and review workstation vendors. Combined with the number of aspects and features of image display, the possible opportunities for defect is on the order of 10,000-1,000,000. Thus, it is difficult to create one comprehensive tool to evaluate the multifaceted nature of testing image display. However, it is highly desirable that a PACS correctly display each modality and each type of LUT, such as VOI-LUT, modality LUT, etc.

As previously mentioned, it is highly desirable to display medical images correctly. Thus, it is useful to know the features and/or behaviors of particular modalities and image display systems. For example, if a particular image display system claims to support a particular LUT, but actually does not implement it as expected by the modality, it may be desirable to detect the actual behavior of the image display system and configure the modality's behavior based on that behavior. As another example, an image display system may not implement a particular feature, and thus it may be desirable to configure the modality to provide images in a different manner to account for the lack of the feature in the image display system.

Current modalities, PACS, and review workstations may provide one or more test patterns. Two common test patterns are the 1985 SMPTE test pattern and the AAPM Task Group (TG) 18 test patterns. These patterns were initially designed for physics evaluations of image display devices, such as monitors.

The SMPTE pattern is often used in the medical imaging field. For example, the SMPTE pattern is included with many current acquisition modalities and image display systems. The SMPTE pattern does not include a LUT. Thus, the SMPTE pattern cannot test aspects of image display relating to LUTs.

The AAPM TG-18 test patterns include many different patterns and clinical images. Each image is a completely separate file from the others. In addition, the TG-18 test patterns do not combine clinical sample images with test patterns. Similar to the SMPTE pattern, the TG-18 test patterns do not include or test LUTs. Further, neither the SMPTE pattern nor the TG-18 pattern was designed for testing clinically relevant image display functionality.

Other standards exist for display monitor evaluation including, for example, the NEMA-DICOM standard part 3.14, the German DIN standard, the ISO 9241 and 13406 series, and the VESA standard. However, these standards focus on monitor evaluation through static, single test patterns. They do not evaluate image display functionality related to PACS and review workstations.

IHE and DICOM Working Group (WG) 11 also provide a series of publications and images that offer functionality and methodology for image display consistency testing. This set of test image patterns provides a series of images to evaluate various LUT combinations (Modality LUT, VOI LUT, and Presentation LUTs); a series of images to evaluate the impact of non-grayscale variations (annotations, shuttering, and spatial transformations); a series of images to evaluate softcopy-to-softcopy consistency, softcopy-to-hardcopy consistency, and hardcopy-to-softcopy consistency; and a test pattern that combines a ramp pattern with a luminance square that can be measured.

However, the IHE test images do not provide a combination of test pattern with a clinical sample image providing simultaneous evaluation of luminance saturation and clinical image display. In addition, the IHE test images do not allow for quantitative comparison of two images for relative comparisons, provide universality of image pixel data, provide a method to test the interactive nature of image display when a user changes the brightness or contrast, or provide asymmetry in the VOI-LUT that helps evaluate whether the LUT is applied correctly.

Thus, there is a need for systems and methods for an interactive PACS image display test image.

BRIEF SUMMARY OF THE INVENTION

Certain embodiments of the present invention provide a test image including a plurality of bands and a plurality of markers in each band. Each band includes a plurality of pixels of the same pixel value. Each marker contrasts with the plurality of pixels in the band. The markers are adapted to allow a user to determine a feature of an image display system.

Certain embodiments of the present invention provide a method for testing image display including receiving a set of test images, displaying a test image from the set of test images with an image display system, adjusting a display characteristic of the image display system, and determining a feature of the image display system based at least in part on the adjustment and the set of test images. The set of test images including a plurality of images.

Certain embodiments of the present invention provide a user interface for testing an image display system including a display adapted to present a test image to a user and a control adapted to adjust a display characteristic of the display. The test image includes a test pattern and a sample image. A feature of the display is determined based at least in part on the adjustment and the test image.

BRIEF DESCRIPTION OF SEVERAL VIEWS OF THE DRAWINGS

FIG. 2 illustrates a flow diagram for a method for testing image display in accordance with an embodiment of the present invention.

Figure 1:
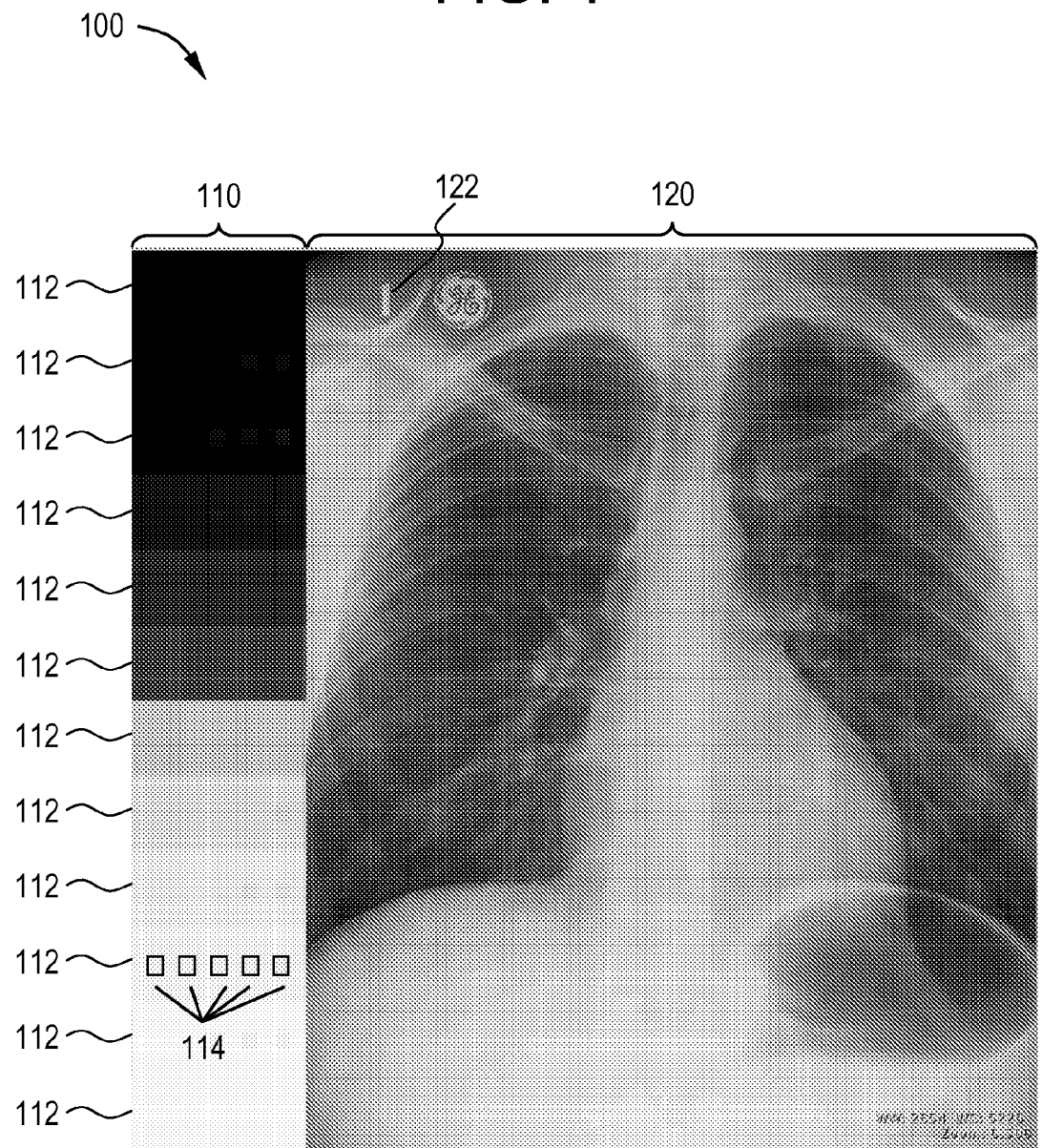
FIG. 1 illustrates a test image according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a test image 100 according to an embodiment of the present invention. The test image 100 includes a test pattern 110 and a sample image 120. The following discussion is with respect to the exemplary grayscale image illustrated in FIG. 1, however, it should be understood that certain embodiments of the present invention may include color.

In certain embodiments, the test pattern 110 is positioned adjacent to the sample image 120. For example, the test pattern 110 may be positioned to the left, right, top, or bottom of the sample image 120. In certain embodiments, the test pattern 110 is positioned near or at the center of the sample image 120. In certain embodiments, the test pattern 110 is positioned on top of the sample image 120. In certain embodiments, the test image 100 does not include a sample image 120.

The test pattern 110 includes two or more bands 112. Each band 112 has a constant pixel intensity. For example, the test pattern 110 may include twelve bands 112, each band 112 with a different pixel intensity from one or more other bands 112, and each pixel within a band 112 of the same pixel value.

Each band includes one or more markers 114. Each marker 114 within a band 112 has an intensity that contrasts with the pixel intensity of the band 112. For example, one marker 114 may have a contrast of 1%, while a second marker 114 in the same band 112 may have a contrast of 5%. The markers 114 may be used as a gauge of the image display functionality, for example.

The sample image 120 may be a clinically relevant sample image, for example. For example, as illustrated in FIG. 1, the sample image 120 includes an postero-anterior (PA) chest radiograph. The sample image 120 may provide clinical significance while the viewer reviews the image on both the acquisition and review workstations, for example. That is, the sample image 120 may provide clinical significance to the measurements and results of the testing, for example. The sample image 120 may allow the numeric metrics to be related to the clinical exams, for example.

In certain embodiments, the sample image 120 includes a watermark image number 122. The watermark image number 122 may indicate the position of the test image 100 in a sequence of images, for example.

In operation, the test image 100 is provided to a display system. The display system may be a PACS workstation, for example. As another example, the display system may be a review workstation.

The test image 100 may be provided by an imaging modality, for example. For example, the test image 100 may be provided to a PACS workstation by a digital x-ray or MR modality. Alternatively, the test image 100 may be provided by a computer-readable storage medium such as a compact disk (CD), hard disk, or flash drive. For example, a user may load the test image 100 from a CD onto a review workstation to perform a test. As another example, the test image 100 may allow a field engineer to configure a modality and/or an image display system to improve operation and/or image display.

The test image 100 may be in a standard image format such as the DICOM format, for example. The test image 100 may utilize one or both of the image pixel data and/or the header tag elements of the DICOM image format, for example.

As mentioned above, the test pattern 110 includes two or more bands 112, each with a constant pixel intensity. The pixel intensities of the bands 112 may range from zero-intensity to full-intensity, for example. In certain embodiments, the pixel intensities of each band 112 are evenly distributed across a range of possible intensity values. For example, if pixel intensity is represented by eight bits, then there are at most 256 potential values, typically ranging from 0 to 255. If there are nine bands, then band one may have pixels of intensity 0, band two may have pixels of intensity 32, band three may have pixels of intensity 64, band four may have pixels of intensity 96, band five may have pixels of intensity 128, band six may have pixels of intensity, 160, band seven may have pixels of intensity 192, and band eight may have pixels of intensity 224, and band nine may have pixels of intensity 255.

In certain embodiments, the test image 100 includes a LUT. The LUT may be included in the image pixel data and/or the header, for example. The LUT may be used to map pixel intensity to a display value. For example, the LUT of the test image 100 may be symmetric. That is, the pixel intensities may be mapped to display values in equal proportion. In certain embodiments of the present invention, the LUT of the test image 100 may be asymmetric. That is, the pixel intensities may not be mapped to display values that are evenly distributed across the total range.

When an asymmetric LUT is applied to bands 112 that have evenly distributed pixel intensities, the displayed values are not evenly distributed. Thus, although 12 bands 112 may be present in the test pattern 110, a user may be able to distinguish a greater number of higher intensity bands 112 than lower intensity bands 112 due to the asymmetric LUT. For example, a user may be able to distinguish 6 "lighter" bands 112, but only 3 or 4 of the "darker" bands 112, even tough the test image 112 may include 6 "darker" bands and 6 "lighter" bands.

Each band 112 may include one or more markers 114. The markers 114 are included within the band 112 and have varying degrees of contrast. For example, each band 112 may include five makers 114, each with a different degree of contrast with respect to the band 112 it is included in. The marker 114 with the lowest contrast may be difficult for a user to see or distinguish. Markers 114 with more contrast may be more easily perceived.

For example, in the test pattern 110 illustrated in FIG. 1, the top and bottom bands have square markers 114 that are of low contrast, less than 1%. These are very difficult for a user to see on most 10-bit image displays. However, when the user changes the brightness and contrast on the display, these 5 square markers 114 can be seen in the top and bottom bands.

The bands 112 and markers 114 in the bands 112 provide an objective mechanism to perform numerous tests on an image display. For example, the bands 112 and markers 114 allow a user to determine whether the LUTs included in the header are being correctly applied. As another example, the bands 112 and markers 114 may be used in an interactive way to demonstrate how a PACS responds when the user makes changes to brightness and contrast.

For example, if the PACS correctly responds to the user changing brightness and contrast, the 5 markers 114 may be seen in the brightest and darkest bands. If the PACS incorrectly responds, and is "not interactive", then the 5 markers 114 in the brightest and darkest bands 112 may not be visible for any combination of brightness and contrast. This is because the LUT is flat for these pixel value ranges. If the LUT is applied to the data, but not updated interactively through either interpolation or functionally, then the data in this region will have no contrast.

As discussed above, the sample image 120 may be a clinically relevant sample image. In certain embodiments, the sample image 120 is of anatomy specific to the modality under analysis. For example, in digital x-ray imaging, the clinical image may be a PA chest radiograph.

The sample image 120 may be selected to highlight and illustrate the image display features of saturation, dynamic range, contrast, noise, and clinical appreciation, for example. For example, the sample image 120 may be an image with a wide dynamic range of intensities. The sample image 120 illustrated in FIG. 1 includes a dark lung region just above the right diaphragm that has vasculature with good contrast. In addition, the sample image 120 also includes a dense white abdomen region in the bottom center of the sample image. This white region has low-contrast vertebrae that extend down through the image.

In certain embodiments, the sample image 120 may be marked with annotations, markers, watermarks, or geometric objects (circles, regions-of-interest (ROIs), etc.), for example. For example, the sample image 120 illustrated in FIG. 1 includes a watermark image number 122 embedded into the pixel intensity. The pixel intensities may be watermarked only slightly so as to not significantly change the image histogram, for example. The watermark image number 122 may be utilized to test the order test images 100 are sent to an image display system, for example. As another example, the watermark image number 122 may be utilized to test the order test images 100 are received at an image display system. As another example, the watermark image number 122 may be utilized to test the order test images 100 are transferred to an image display system.

In certain embodiments, the test image 100 is modular in that it provides several simultaneous troubleshooting tools. The test image 100 may have several aspects in each image, such as a test pattern 110 including bands 112 and markers 114, a sample image 120, and annotations. For example, a test may determine whether the image display system supports the display LUT included in the DICOM header. As another example, a test may determine whether the image display system correctly displays an image independent of annotations, multiple LUTs, the values displayed to the user, and/or modality type. As another example, a test may determine whether the image display system can interactively display an image when the user changes brightness and contrast. That is, does the image display system apply a LUT interactively or non-interactively.

In certain embodiments of the present invention, a set of two or more test images 100 may be utilized to test one or more features of an image display system. For example, the test image 100 may be replicated 9 or 10 or more times resulting in multiple instances of the same image. The sample image 120 pixel data and the test pattern 110 may be identical for each image instance, for example. The instances may differ in features and purposes. For example, the instances may differ in the way in which the test image 100 is sent to the image display system, the DICOM header of the test image 100, the annotations or markers on the test image 100, the watermark image number in the sample image 120, and/or the way in which the image display system is configured when the test image 100 is sent. One of the test images may be a baseline image, for example. The baseline image may be used as a control image for comparing to other test images 100 to test one or more features of an image display system. Table 1 below illustrates several exemplary configurations of test images 100 in a set of test images along with a use case for the test image 100.

TABLE 1

List of image instances.

| # | Send Method | Purpose |
|---|---|---|
| 1 | LUT in Header | Baseline, system default settings. |
| 2 | LUT in Header | Identical to #1, used to test different PACS settings/options |
| 3 | LUT in Header | Identical to #1, used to test interactive display |
| 4 | LUT in Header | Test impact of text annotations |
| 5 | LUT in Header | Test impact of annotations burned into pixel data |
| 6 | LUT Burned into pixels | Compare to image #1 to test how PACS applies LUT |
| 7 | LUT Burned into pixels | Test impact of text annotations |
| 8 | LUT Burned into pixels | Test impact of annotations burned into pixel data |
| 9 | LUT Burned into pixels when sent as different modality | Test sending images as CR-modality |
| 10 | LUT in Header | Used to test Multiple-LUTs included in header |

Other test images 100 may be included to test other features such as collimation, image size, or other image header features, for example.

In certain embodiments, the test image 100 employs an asymmetric LUT. The asymmetry of the embedded LUT enables evaluation of the method the image display system employs to apply the LUT and display the resulting data. For example, if the PACS workstation fails to use the asymmetric VOI-LUT, as indicated by displaying the test image 100, then imaging modality may be configured to use a symmetric, linear LUT.

In certain embodiments, the test image 100 employs the concept of universality. That is, the test pattern 110 and sample image 120 have identical pixel values for each image instance. The theory for these images is that every instance, if displayed correctly, will result in an identical image when viewed on an image display system.

In certain embodiments, the test image 100 employs the concept of counterweight. That is, the test image 100 may be used regardless of image display system monitor calibration. Thus, the test images 100 are a relative, quantitative comparison tool, so conclusions are based on comparisons of one image instance to another, regardless of monitor calibration.

In certain embodiments, the test image 100 may be inverted. Tests may then be repeated for image inversion. Image inversion is another criteria and feature typically used clinically.

In certain embodiments, the test image 100 may require the operator to change the image brightness and contrast to test for interactive application of LUTs. That is, the user may display the test image 100 and then adjust the brightness and/or contrast on the image display system to determine if a LUT is correctly reapplied.

In certain embodiments, an image number watermarks may help test and troubleshoot issues with the order of image send, order of image receive, and order of image display. Image transfer between modality and image display system often encounters issues with image order. Image order may be important in situations such as the use of a hanging protocol, for example.

FIG. 2 illustrates a flow diagram for a method 200 for testing image display in accordance with an embodiment of the present invention. The method 200 includes the following steps, which will be described below in more detail. At step 210, a set of test images is received. At step 220, a test image is displayed. At step 230, a display characteristic is adjusted. At step 240, a feature is determined based at least in part on the adjustment. The method 200 is described with reference to elements of systems described above, but it should be understood that other implementations are possible.

At step 210, a set of test images is received. The set of test images may include one or more test images. The test images may be similar to the test image 100, described above, for example. The set of test images may be utilized to test one or more features of an image display system, for example.

The test image may be received from an imaging modality, for example. For example, a PACS workstation may receive the test image from a digital x-ray or MR modality. Alternatively, the test image may be received from a computer-readable storage medium such as a CD, hard disk, or flash drive. For example, the test image may be received from a user loading the test image from a CD.

At step 220, a test image is displayed. The test image may be a test image in the set of test images received at step 210, described above, for example. The test image may be displayed on a display, for example. The display may be part of an image display system, such as a PACS or review workstation, for example.

At step 230, a display characteristic is adjusted. The display characteristic may include brightness and/or contrast, for example. The display characteristic may be adjusted by a user, for example. Alternatively, the adjustment may include displaying another test image from the received set of test images.

At step 240, a feature is determined based at least in part on the adjustment. The feature may be determined by a user, for example. The adjustment may be the adjustment made at step 230, described above, for example.

The feature may be determined based on an observed effect of the display of the test image displayed at step 220, described above, for example. For example, the test image may include bands and markers in the bands adapted to provide an objective mechanism to perform numerous tests on an image display. The bands may be similar to the bands 112, described above, for example. The markers may be similar to the markers 114, described above, for example.

For example, the bands and markers may allow a user to determine whether a LUT included in the header of the test image is being correctly applied. As another example, the bands and markers may be used in an interactive way to demonstrate how an image display system responds when the user makes changes to brightness and contrast.

For example, if a PACS correctly responds to the user changing brightness and contrast, the markers may be seen in the top and bottom bands. If the PACS incorrectly responds, and is "not interactive", then the markers in the top and bottom bands may not be visible for any combination of brightness and contrast.

As another example, the set of test images may include 9 or 10 instances of the test image. The sample image pixel data and the test pattern may be identical for each image instance, for example. The instances may differ in features and purposes. For example, the instances may differ in the way in which the test image is sent to the image display system, the DICOM header of the test image, the annotations or markers on the test image, the watermark image number in the sample image, and/or the way in which the image display system is configured when the test image is sent. One of the test images may be a baseline image, for example. The baseline image may be used as a control image for comparing to other test images 100 to test one or more features of an image display system. Table 1 above illustrates several exemplary configurations of test images 100 in a set of test images along with a use case for the test image 100.

Other test images may be included to test other features such as collimation, image size, or other image header features, for example.

In certain embodiments, a test image in the set of received test images employs an asymmetric LUT. The asymmetry of the embedded LUT enables evaluation of the method the image display system employs to apply the LUT and display the resulting data. For example, if the PACS workstation fails to use the VOI-LUT, as indicated by displaying the test image, then imaging modality may be configured to apply the LUT before sending images to another workstation and/or PACS.

In certain embodiments, the one or more of the received test images may be marked with annotations, markers, watermarks, or geometric objects (circles, regions-of-interest (ROIs), etc.), for example. For example, each test image may include a watermark image number similar to watermark image number 122, described above. The watermark image number 122 may be utilized to test the order test images 100 are sent to an image display system, for example. As another example, the watermark image number 122 may be utilized to test the order test images 100 are received at an image display system. As another example, the watermark image number 122 may be utilized to test the order test images 100 are transferred to an image display system.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide systems and methods for an interactive PACS image display test image. Certain embodiments provide the technical effect of an interactive PACS image display test image While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A processor configured to display a test image on an image display system, wherein the test image comprises:
   a sample image displayed according to a look-up table;
   a test pattern displayed along with the sample image and including a plurality of bands displayed according to the look-up table, wherein each band has a different intensity; and
   a plurality of markers included within a first band of the plurality of bands, wherein each marker has a different intensity that contrasts the intensity of the first band, and wherein each marker has a different degree of contrast with respect to the first band,
   wherein each marker is configured to change its degree of contrast according to at least one of a brightness or a contrast of the image display system, and
   wherein the sample image comprises a clinical radiological image.

2. The processor of claim 1, wherein the test image comprises a header including the look-up table.

3. The processor of claim 1, wherein the look-up table is asymmetric.

4. The processor of claim 1, wherein the test image comprises a watermark adapted to test at least one of an image send order, a receive order, or a transfer order.

5. A method for testing an image display system and to be performed by the image display system, wherein the method comprises:
   receiving a set of test images;
   displaying a first test image from the set of test images with an image display system according to a look-up table, wherein the first test image includes a sample image and a plurality of bands;
   displaying a plurality of markers within a first band of the plurality of bands, wherein each of the plurality of markers has a different intensity that contrasts the intensity of the first band, and wherein each marker has a different degree of contrast with respect to the first band; and
   adjusting at least one of a brightness or a contrast of the image display system to improve a visibility of each of the plurality of markers within the first band,
   wherein the sample image comprises a clinical radiological image.

6. The method of claim 5, wherein the set of test images is adapted to test at least one of an image send order, a receive order, or a transfer order.

7. A non-transitory computer readable medium including a set of instructions, the set of instructions including:
   a reception routine for receiving a set of test images;
   a display routine for displaying a first test image from the set of test images with an image display system, wherein the first test image includes a sample image and a plurality of bands;
   a display routine for displaying a plurality of markers within a first band of the plurality of bands, wherein each of the plurality of markers has a different intensity that contrasts the intensity of the first band, and wherein each marker has a different degree of contrast with respect to the first band; and
   an adjustment routine for adjusting at least one of a brightness or a contrast of the image display system to improve a visibility of each of the plurality of markers within the first band, and
   wherein the sample image comprises a clinical radiological image.

8. The processor of claim 1, wherein a first marker of the plurality of markers is discernable within the first band at a first brightness and contrast, and
   wherein the first marker is not discernable within the first band at a second brightness and contrast.

9. The processor of claim 1, wherein an intensity of a first marker of the plurality of markers contrasts the intensity of the first band by less than one percent.

* * * * *